United States Patent [19]

De Micheli et al.

[11] 4,390,727

[45] Jun. 28, 1983

[54] PROCESS FOR PREPARING STABLE AQUEOUS SUSPENSIONS OF FORMALDEHYDE

[75] Inventors: Angelo De Micheli, Saronno; Piero Bizzozero, Samarate, both of Italy

[73] Assignee: Montedison S.p.A., Milan, Italy

[21] Appl. No.: 288,116

[22] Filed: Jul. 29, 1981

[30] Foreign Application Priority Data

Nov. 19, 1976 [IT] Italy ................................ 29549 A/76

[51] Int. Cl.$^3$ ............................................ C07C 47/058
[52] U.S. Cl. ..................................................... 568/422
[58] Field of Search ........................................ 568/422

[56] References Cited

U.S. PATENT DOCUMENTS

| | | | |
|---|---|---|---|
| 3,379,769 | 4/1968 | Prinz et al. | 568/422 |
| 3,423,467 | 1/1969 | Dakli et al. | 568/422 |
| 3,770,830 | 11/1973 | Reni et al. | 568/422 |

FOREIGN PATENT DOCUMENTS

| | | | |
|---|---|---|---|
| 1070611 | 1/1958 | Fed. Rep. of Germany | 568/422 |
| 1213829 | 4/1966 | Fed. Rep. of Germany | 568/422 |
| 1245351 | 7/1967 | Fed. Rep. of Germany | 568/422 |
| 1268608 | 5/1968 | Fed. Rep. of Germany | 568/422 |
| 2061258 | 6/1972 | Fed. Rep. of Germany | 568/422 |
| 1386656 | 12/1965 | France | 568/422 |
| 41-11851 | 6/1966 | Japan | 568/422 |
| 968762 | 9/1964 | United Kingdom | 568/422 |
| 1029039 | 5/1966 | United Kingdom | 568/422 |
| 1063541 | 3/1967 | United Kingdom | 568/422 |
| 1175560 | 12/1969 | United Kingdom | 568/422 |

*Primary Examiner*—Werren B. Lone

[57] ABSTRACT

Stable aqueous suspensions of formaldehyde of at least 40% by weight concentration are prepared by heating aqueous formaldehyde solutions to a temperature of from about 40° C. to about 80° C. in the presence of stabilizing agents, in the presence or absence of methanol, and at a pH in the range of from about 0.5 to 1.5 or about 6.0 to about 8.0, cooling the mass to a temperature of from about 10° C. to about 40° C., and adjusting the pH thereof to about 3.0 to 4.0.

16 Claims, No Drawings

PROCESS FOR PREPARING STABLE AQUEOUS SUSPENSIONS OF FORMALDEHYDE

This is a Continuation-in-part of our application Ser. No. 105,874 filed Dec. 21, 1979, which was a Rule 60 Continuation of our application Ser. No. 22,465 filed Mar. 21, 1979 (now abandoned) in its turn a Rule 60 Continuation of our application Ser. No. 852,721 filed Nov. 18, 1977, (now abandoned).

THE PRIOR ART

Up until now, and in order to cope with the practical problems of transportation, storage, handling, etc., all of which are important to the industrial use of formaldehyde, the art has been concerned with processes for providing aqueous solutions of formaldehyde of the highest possible concentration and stable over the widest possible temperature range, taking account of the fact that, as is well-known, formaldehyde in aqueous solution readily undergoes polymerization, forming polymers (paraformium) which precipitate, separate out, in a substantially irreversible way.

So far as is known to applicants, the prior art is unanimous in describing methods for stabilizing aqueous solutions of formaldehyde by the addition thereto of stabilizing agents such as methanol, melamine, guanamine, urea, etc., and more or less complicated derivatives of said additives, under particular parameters of concentration, temperature, etc., and has been concerned with insuring the absence of formaldehyde in suspension and of turbidity due to formaldehyde polymerization.

Also, so far as is known to applicants, the art does not describe aqueous formaldehyde suspensions obtained industrially and industrially useful, or methods for obtaining such suspensions.

On the other hand, the advantages, economical and applicative, of having available aqueous formaldehyde solutions which are industrially usable as such, are evident.

THE PRESENT INVENTION

One object of this invention is to provide aqueous formaldehyde suspensions which have the same industrial uses as the aqueous formaldehyde solutions of the prior art, stabilized or not, and, for instance, in the preparation of synthetic resins, tanning agents, dyestuffs, etc.

Another object is to provide a simple and economical method for preparing the industrially new aqueous formaldehyde suspensions.

These and other objects are achieved by the present invention in accordance with which stable aqueous formaldehyde suspensions are prepared by bringing aqueous formaldehyde solutions to a temperature comprised between 40° C. and about 80° C., in the presence of conventional stabilizing agents and at a pH comprised in a range selected between the range of 0.5 to 1.5 and 6.0 to about 8.0, cooling the mass to a temperature comprised between about 10° C. and about 40° C., and adjusting the pH thereof to a value comprised between about 3.0 and 4.0.

Depending on the concentration of formaldehyde in the starting aqueous solution, and the predetermined temperature and pH conditions, the aqueous formaldehyde suspensions thus obtained contain from 5% to about 25% by weight of formaldehyde polymer in suspension and in substantially re-dissolvable form, by simple addition of water and/or warming to a substantially neutral pH, stirring etc.

The suspensions are useful for all of the uses, in general, for which the aqueous formaldehyde solutions are used.

The present process allows precipitation, under controlled conditions, of part of the formaldehyde present in concentrated aqueous solutions, resulting in stable aqueous suspensions of low polymers of a high degree of solubility, in which suspensions the clear phase has a lower formaldehyde concentration and therefore involves less stabilization problems, while the total amount of formaldehyde present in the same volume of water remains constant.

For instance, from aqueous solutions containing formaldehyde in a concentration of 50%, and which, as solutions, normally present serious stabilization problems, it is possible, proceeding according to this invention, to obtain suspensions the clear phase of which contains formaldehyde in a concentration of about 40% which is easily stabilized by means of conventional stabilizing agents and containing suspended polymer, stable in time, such as to bring the overall titration to the original 50%.

The limits on the concentration of formaldehyde in the aqueous suspensions are set, on the one hand, and so far as concerns the lower limit, by the ease of obtaining stable aqueous starting solutions when the formaldehyde concentration is relatively low, and, on the other hand, and so far as concerns the upper limit, by the need to avoid liquids of too high viscosity for use in pumping, various transferring operations, etc. For practical, industrial purposes, the suspensions comprise between 40% and about 60% by weight of total formaldehyde.

As indicated, the starting aqueous formaldehyde solution, at a temperature comprised between about 40° C. and 80° C., preferably at about 50° C., is brought to a pH comprised in the range of 0.5 to 1.5 or, alternatively, in the range of about 6.0 to about 8.0, preferably between 6.5 and 7.0, in the presence of conventional stabilizers.

The pH adjustment is by the addition of alkaline agents, e.g., NaOH, etc., or of acids, e.g., $H_2SO_4$, etc., or by deacidification, for instance by means of exchange resins, etc.

As stabilizers of the starting aqueous solutions there may be used practically all of the stabilizers used conventionally, and in particular alkyl or aryl guanamines, or derivatives thereof.

The stabilizing agents act substantially on the clear phase (solution) of the suspensions obtained.

In practice, the initial heating of the formaldehyde solution is carried out at a temperature comprised between about 40° C. and 80° C., preferably at about 50° C., and the solution is maintained at the selected temperature for a time which may vary inversely with the temperature between about 4 hours and 30 minutes, but is preferably about 2 hours.

After cooling to about 10° C. to 40° C., the pH is adjusted to a value of from 3.0 to 4.0 by the addition of organic acids, such as formic acid, acetic acid, etc., or of alkaline agents, e.g., NaOH, carbonates, etc., respectively, and depending on the initial range of pH selected.

Protective colloids, such as polyvinyl alcohol, etc., may be added in amounts of e.g., 100 to 1,500 p.p.m. and according to known techniques, for improving the overall stability.

The aqueous formaldehyde suspensions of the invention are stable and useful at temperatures above about 15° C. and for a time not less than seven days.

The process of the invention is simple and has the additional advantage that it is possible to dispose, at equal occupied volumes, of a greater quantity of formaldehyde in a form ready for direct use, with consequent operating and economic benefits, than is possible with the aqueous formaldehyde solutions heretofore available. Other advantages of the invention include the easier stabilization of the aqueous formaldehyde in the suspension form, and the relatively low cost and practicality of the handling, storing, and operations involving use of the suspension in industrial applications.

The following examples are given to illustrate the invention in more detail and are not intended to be limiting.

EXAMPLE 1

1000 g of an aqueous solution of formaldehyde at a concentration of 50% were brought up to 50° C. and then additioned with 0.6 g of benzoguanimine and 0.5 g of polyvinyl alcohol. This mixture was maintained at 50° C. for about 2 hours, under stirring. It was then adjusted to a pH equal to 7 by the addition of sodium hydrate. Thereupon, the solution was allowed to cool down to 25° C. under stirring, and then maintained at that temperature for 12 hours. Thereafter, the solution was adjusted to a pH equal to 3.5 by the addition of formic acid.

A fluid suspension having a viscosity of 40 cP at a temperature of 20° C. was obtained. It remained stable for a period of at least 30 days at a temperature of 25° C.

EXAMPLE 2

To 1,000 g of a formaldehyde solution at 45% by weight concentration, brought up to a temperature of 50° C., were added 0.5 g of benzoguanamine and 0.4 g of polyvinyl alcohol. This solution was kept under slow stirring for three hours at a temperature of 46° C. Thereupon, it was brought up to a pH equal to 6.8 by the addition of sodium hydrate. The solution was then cooled down to a temperature of 15° C. and was maintained at that temperature under stirring for 16 hours. Thereafter the pH was brought to 3.6 by the addition of formic acid.

A fluid suspension having a viscosity of 35 cP at 20° C. was obtained. It remained stable for a period of at least 30 days at a temperature of 20° C.

EXAMPLE 3

To 1,000 g of a formaldehyde solution at a 55% by weight concentration, brought up to a temperature of 60° C., were added 0.8 g of benzoguanamine and 0.6 g of polyvinyl alcohol. The solution was then maintained for two hours under stirring at a temperature of 60° C., after which the pH was adjusted to 7 by the addition of sodium hydrate. The solution was then cooled down to a temperature of 35° C. and maintained at that temperature under stirring for 12 hours. Thereafter, the pH was brought to 3.5 by the addition of formic acid.

A fluid suspension having a viscosity of 42 cP at 20° C. was obtained. It remained stable for a period of at least 30 days at a temperature of 20° C.

EXAMPLE 4

To 1,000 g of an aqueous formaldehyde solution at a 50% by weight concentration brought to a temperature of 50° C., were added 0.1 g of m-phthalo-bis-guanamine and 0.5 g of polyvinyl alcohol. This solution was kept under stirring at 50° C. for two hours. The pH was then brought to 7 by the addition of sodium hydrate, after which the solution was cooled down to 25° C. and maintained at 25° C. under stirring for 12 hours. The pH was then brought to 3.5 by the addition of formic acid.

Thereby was obtained a fluid suspension having a viscosity of 40 cP at 20° C. It remained stable for a period of at least 10 days at 20° C.

EXAMPLE 5

To 1,000 g of an aqueous formaldehyde solution at a 50% by weight concentration, brought to a temperature of 50° C., were added 0.1 g of lauroguanamine and 0.5 g of polyvinyl alcohol. The obtained solution was kept under stirring at 50° C. for two hours, after which the pH was brought to 7 by the addition of sodium hydrate. The solution was then cooled down to 30° C. and maintained at 30° C. under stirring for 12 hours, whereupon the pH was adjusted to 3.5 by the addition of formic acid.

The fluid suspension having a viscosity of 46 cP at 20° C. thus obtained remained stable for period of at least 12 days at 20° C.

EXAMPLE 6

1,000 g of a formaldehyde solution at a 50% by weight concentration were brought up to 50° C. and then additioned with 0.6 g of benzoguanamine and 0.5 g of polyvinyl alcohol. The solution was then subjected to stirring for 2 hours at 50° C., after which the pH was brought to the value of 1 by the addition of sulphuric acid. Thereafter, the solution was cooled down to 25° C. under stirring and maintained at that temperature for 15 hours. The pH was then brought to 3.2 by the addition of sodium hydrate. Thereby was obtained a fluid suspension having a viscosity of 48 cP at 20° C., and which was stable for at least 20 days at a temperature of 20° C.

EXAMPLE 7

A formaldehyde solution at 36% by weight concentration was deacidified on exchange resin type A 101 at a temperature of 35° C. and concentrated to a 50% concentration, thereby obtaining a solution having a pH of 6.5.

To 1,000 g of this formaldehyde solution at 50% concentration, brought to 50° C., were added 0.6 g of benzoguanamine and 0.5 g of polyvinyl alcohol. The temperature was maintained at 50° C. while stirring for two hours. The pH proved to be 6.5 and this value was then brought to a pH=7.3 by the addition of NaOH. Thereupon, the solution was cooled down to 25° C. under stirring and was maintained at that temperature for 15 hours. Thereafter the pH was brought to 3.5 by the addition of formic acid thereby obtaining a suspension having a viscosity of 50 cP at 20° C.

This suspension remained stable for at least 30 days at a temperature of 25° C.

EXAMPLE 8

1,000 g of a solution containing 50% by weight of formaldehyde and having a pH of 2.8, were brought to 40° C.; then 0.5 g of benzoguanamine and 0.5 g of polyvinylalcohol were added.

The temperature was kept at 40° C. for 2 hours under stirring, whereupon the pH was brought to 7.0 by addition of sodium hydrate. The whole was then cooled down to 25° C. under stirring and was kept at such temperature for 20 hours. By adding formic acid the pH was brought to 3.6 and a fluid suspension having a viscosity of 46 cP at 20° C., stable for a period of at least 30 days at 20° C. was obtained.

EXAMPLE 9

1,000 g of a solution containing 50% by weight of formaldehyde and having a pH of 3.0 were brought to 80° C.; then 0.6 g of benzoguanamine and 0.5 g of polyvinyl alcohol were added.

The temperature was kept at 80° C. for 2 hours under stirring and the pH was brought to 7.0 by addition of NaOH. The whole was cooled down to 25° C. under stirring and maintained at such temperature for 20 hours, whereupon the pH was brought to 3.4, by addition of formic acid, and a fluid suspension having a viscosity of 42 cP at 20° C. and stable for at least a 25-day period at 20° C. was thus obtained.

EXAMPLE 10

1,000 g of a solution containing 50% by weight of formaldehyde and having a pH of 2.7 were percolated on an anionic exchange resin (Kastel A101) at a temperature of 50° C.

The solution obtained after having conveyed the same over the resin had a pH of 7.0. This solution, always maintained at 50° C., was additioned with 0.6 g of benzoguanamine and 0.5 g of polyvinyl alcohol.

The temperature was kept for 2 hours at 50° C. under stirring. The pH was then brought to 8.0 by addition of NaOH. The whole was cooled down to 25° C. under stirring and kept at such temperature for 20 hours. The pH was successively brought to 3.5 by addition of formic acid. A fluid suspension having a viscosity of 45 cP at 20° C. and stable for at least an 18-day period at 20° C. was so obtained.

EXAMPLE 11

1,000 g of a solution containing 50% by weight of formaldehyde and having a pH of 2.7 were treated on a resin as described in Example 10. The pH had a value of 6.5.

At a temperature of 50° C., 0.6 g of benzoquanamine and 0.5 g of polyvinyl alcohol were added to the solution, which was then stirred for 2 hours at 50° C. By addition of NaOH the pH was then brought to 7.3. The whole was cooled to 25° C. under stirring and was kept for 20 hours at such temperature. The pH was then brought to 3.5 by addition of formic acid. A fluid suspension having a viscosity of 50 cP at 20° C., stable for at least a 27-day period at 20° C. was obtained.

EXAMPLE 12 (Comparative)

1,000 g of a solution containing 50% by weight of formaldehyde, having a pH equal to 2.6, were brought to 50° C. and additioned with 1.5 g of benzoguanamine. The whole was stirred for 2 hours always at 50° C. and then brought to pH of 6.0 by addition of sodium hydrate. Successively the solution was cooled down to 25° C. under stirring and maintained at such temperature for 20 hours. The pH was then brought to 3.6, by addition of formic acid, and a fluid suspension having a viscosity of 50 cP at 20° C. was obtained.

Notwithstanding the fact that the amount of benzoguanamine had been trebled, with respect to Example 8, and that the temperature of the heat treatment was raised to 50° C., the suspension was stable for a period of only 8 days at a temperature of 20° C.

As shown in Example 8, a temperature as low as 40° C. is sufficient for obtaining optimum results, although as shown by Example 9 a temperature of 80° C., which may be regarded as the upper temperature limit, can also be used.

Examples 10 and 11 illustrate use of an exchange resin as pH-modifying means.

Comparative Example 12 establishes the criticality of using the synergistic combination of the guanaminic and polyalcoholic stabilizers, in that it shows the poor results obtained when the guanaminic stabilizer is used alone.

The amount of solids in the suspensions is determined as follows:

The suspension is poured into a 25 cc test tube, the tube is placed in a centrifuge, and the apparatus is run for 30 minutes at a speed of 3,000 rpm. The limpid layer thus obtained is removed by means of a pipette, acetone is then poured into the test tube, which is agitated in order to suspend the solids in the acetone.

The centrifugation is repeated, acetone is removed by means of a pipette, and the wet solid is transferred, with the aid of more acetone, to a 50 cc glass flask.

The whole is dried under vacuum (residual pressure=50 mm Hg) at a temperature not higher than 30° C. Finally, the dry residue is weighed.

What is claimed is:

1. A stable, fluid and homogeneous suspension, containing from 40 to 60% by weight of formaldehyde in water, in which a portion of the formaldehyde is present in the form of soluble monomer and/or oligomers, the remnant of the formaldehyde, amounting to 5 to 25% by weight, with respect to the whole suspension, being present in the form of undissolved but thermally re-dissolvable polymers of the formaldehyde, which polymers do not settle after at least ten days at temperatures equal to or higher than 20° C., said suspension being obtained by heating a starting aqueous solution, containing from 40 to 60% by weight of formaldehyde at temperatures from 40° to 80° C. under stirring, then admixing with it, at such temperatures, a stabilizing combination of polyvinyl-alcohol and of a guanamine selected from the group consisting of benzoguanamine, m-phthalo-bis-guanamine and lauroguanamine, adjusting the pH to a value from 0.5 to 1.5 or from 6.0 to 8.0, cooling the mixture to a temperature from 10° to 40° C., maintaining such cooled mixture under stirring for a time comprised between 4 and 24 hours, and finally adjusting the pH of the cooled mixture between 3.0 and 4.0.

2. A stable suspension according to claim 1, in which said polymers do not settle for at least 30 days at temperatures equal to or higher than 20° C.

3. A process for preparing stable, fluid and homogeneous suspensions of formaldehyde in water, said process comprising healing a starting aqueous solution containing from 40 to 60% by weight of formaldehyde at temperatures from 40° to 80° C. under stirring, then admixing with it, at such temperatures, a stabilizing combination of polyvinyl-alcohol and a guanamine selected from the group consisting of benzoguanamine, m-phthalo-bis-guanamine and lauroguanamine, adjusting the pH of the mixture to a value from 0.5 to 1.5 or from 6.0 to 8.0, cooling the mixture to a temperature from 10° to 40° C., maintaining such cooled mixture under stirring for a time comprised between 4 and 24 hours, and finally adjusting the pH of the cooled mixture to between 3.0 and 4.0, to obtain a stable, fluid and homogeneous suspension.

4. The process according to claim 3, in which the starting aqueous solution contains from 50 to 60% by weight of formaldehyde.

5. The process according to claim 3, in which the starting aqueous solution is heated at a temperature from 50° to 80° C.

6. The process according to claim 3, in which the pH of the solution containing the stabilizing combination of polyvinyl alcohol and guanamine is adjusted to a value from 6.5 to 7.0.

7. The process of claim 3, wherein the final pH is adjusted between 3 and 4 by addition of an organic acid.

8. The process of claim 7, in which the organic acid is formic acid or acetic acid.

9. The process of claim 3, in which the pH of the starting aqueous solution is adjusted, before cooling, between 6.0 and 8.0 or between 0.5 and 1.5 by deacidification with ion-exchange resins or by the addition of, respectively, alkaline agents or acids.

10. The process of claim 9, in which the alkaline agent is NaOH.

11. A stable suspension according to claim 1, in which, in the stabilizing combination with polyvinyl alcohol, the guanamine is benzoguanamine.

12. A stable suspension according to claim 1 in which, in the stabilizing combination with polyvinyl alcohol, the guanamine is m-phthalo-bis-guanamine.

13. A stable suspension according to claim 1 in which, in the stabilizing combination with polyvinyl alcohol, the guanamine is lauroguanamine.

14. The process of claim 3, in which, in the stabilizing combination with polyvinyl alcohol, the guanamine is benzoguanamine.

15. The process of claim 3 in which, in the stabilizing combination with polyvinyl alcohol, the guanamine is m-phthalo-bis-guanamine.

16. The process of claim 3 in which, in the stabilizing combination with polyvinyl alcohol, the guanamine is lauroguanamine.

* * * * *